United States Patent [19]

Martin

[11] Patent Number: 5,147,303

[45] Date of Patent: Sep. 15, 1992

[54] DISPOSABLE SAFETY SYRINGE

[76] Inventor: Bret C. Martin, 2001 Range Ave. No. 62, Santa Rosa, Calif. 95401

[21] Appl. No.: 704,395

[22] Filed: May 23, 1991

[51] Int. Cl.⁵ .............................................. A61M 5/00
[52] U.S. Cl. .................................. 604/110; 604/198; 604/263
[58] Field of Search ............... 604/110, 198, 263, 192, 604/187

[56] References Cited

U.S. PATENT DOCUMENTS

| | | | |
|---|---|---|---|
| 4,795,432 | 1/1989 | Karczmer | 604/110 |
| 4,826,489 | 5/1989 | Haber et al. | |
| 4,850,968 | 7/1989 | Romano | 604/110 |
| 4,850,977 | 7/1989 | Bayless | |
| 4,863,434 | 9/1989 | Bayless | |
| 4,927,416 | 5/1990 | Tomkiel | 604/198 |
| 4,935,016 | 6/1990 | Deleo | |
| 4,950,250 | 8/1990 | Haber et al. | |
| 5,024,616 | 6/1991 | Ogle, II | 604/192 |
| 5,026,353 | 6/1991 | Bartman | 604/192 |

Primary Examiner—John D. Yasko
Attorney, Agent, or Firm—Richard C. Litman

[57] ABSTRACT

Disclosed is a conventional syringe held within a sheath against the bias of a compression spring by a latch engaging an upper end of the compression spring which is also attached to an upper flange of the cylinder of said syringe. The lower end of said spring is attached to a rubber gasket or o-ring which is also attached to said sheath. At the lower end of the sheath is an opening for a needle which may be sealed by a pivoted spring biased disc when the needle is withdrawn into the sheath. The gasket and disc may include spongy material to absorb any liquid which may leak from the needle after withdrawal into the sheath. When the needle is to be disposed of, the syringe is depressed far enough to cam the latch out of engagement with the upper end of said compression spring enabling said compression spring to raise said syringe relative to said sheath enough to withdraw said needle into said sheath, thereby sealing the needle without subjecting the user to accidental pricks.

5 Claims, 3 Drawing Sheets

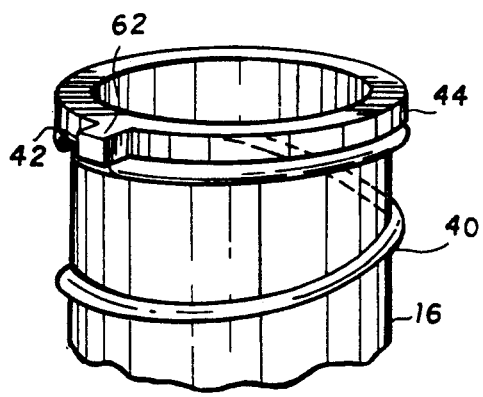
FIG. 5
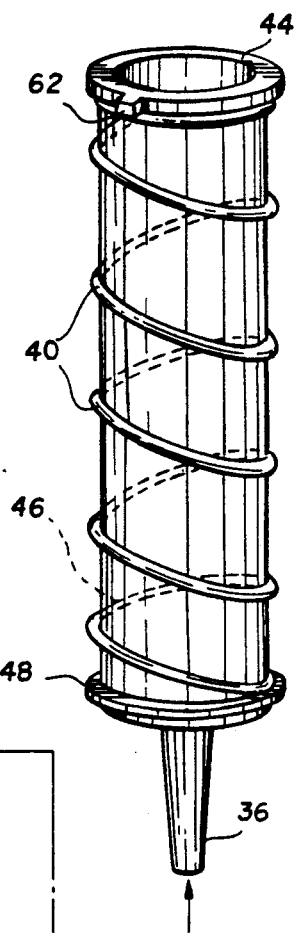
FIG. 4
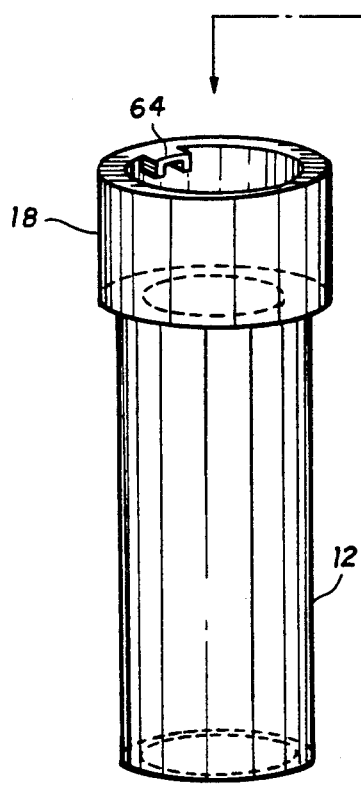

DISPOSABLE SAFETY SYRINGE

BACKGROUND OF THE INVENTION

1. Field of the Invention

This invention relates to a disposable safety syringe provided with a means for withdrawing the needle cannula into a protective sheath which becomes sealed at both ends so as to avoid potentially dangerous contact with the needle tip or with any fluids remaining in the syringe.

In many cases, the syringe may be used to treat a patient having a communicable disease. In the past, prior to disposing the syringe, the hypodermic needle was frequently broken or destroyed to prevent use. In the more recent past, a critical problem has occurred as a result of the rise of such diseases as Acquired Immune Deficiency Syndrome or AIDS in the general populace of patients being administered to by the medical profession. Members of this profession are especially susceptible to accidental and potentially infectious needle strikes due to the careless handling or breaking of the needle prior to disposing the syringe after use. Each inadvertent prick now has the potential of passing a highly contagious and even fatal disease to the medical professional.

The care and attention with which medical professionals perform their tasks are insufficient to safeguard their health and their lives in every situation. Of particular concern are emergency room situations wherein a medical team of professionals work under traumatic conditions. Such a situation invariably leads to accidental stabs with used hypodermics. Hand-manipulated needle sheaths are generally ignored in such situations. There is a need for a simple, quick and expeditious way to protect the medical profession from such accidental stabs by used needles and from contact with body fluids which may remain in syringes after use.

2. Description Of Related Prior Art

A number of devices are known in the prior art which serve the purpose of protecting the user of syringes from accidental pricks or stabs by the needle after use. Most of these devices are too complicated for effective use during emergencies, often requiring the user to place his or her hand in the area of the needle in order to activate the safety devices. While the known devices can be effective to seal off the needle end of the syringe from accidental contact once the safety device is activated, none of the known devices also protect the user from possible contact from body fluids which may leak from the syringe after use even though the needle end is properly covered with a protective sheath.

U.S. Pat. No. 4,826,489, issued May 2, 1989, to Terry M. Haber, Clark B. Foster and William H. Smedley, disclose a disposable safety syringe having means for retracting its needle cannula into its medication cartridge after use by stabbing a double ended needle with the syringe plunger and then withdrawing the plunger with the needle into a substantially empty medication cartridge. The operation requires the use of both hands of the user with no guarantee that body fluids in the syringe have in fact been sealed off.

U.S. Pat. No. 4,850,977, issued Jul. 25, 1989 to William B. Bayless, discloses a button activated automatic sheath for a disposable syringe. As disclosed, the arrangement requires two hands to operate, with one hand being placed near the needle tip in order to operate a button to release a latch holding a spring activated sheath in the inoperative position. Upon release of the latch the sheath moves forward relative to the remainder of the syringe to cover the needle and to close a needle opening in the sheath. There is no showing of any sealing means to prevent contact with body fluids which may leak from the syringe around a support chamber thereof upon which the sheath slides during the needle covering operation.

U.S. Pat. No. 4,863,434, issued Sep. 5, 1989 to William B. Bayless discloses an automatic needle sheath for a disposable syringe Wherein the sheath is spring biased to cover the needle end when sufficient pressure is exerted against the syringe plunger to disengage the sheath from the primary syringe barrel.

U.S. Pat. No. 4,935,016, issued Jun. 19, 1990 to John Deleo, discloses a syringe having two alternate embodiments for covering a needle subsequent to use, both of which involve a two hand operation with one of the hands being in the vicinity of the needle, thereby increasing the chances of accidentally being pricked by the needle. Similarly, U.S. Pat. No. 4,950,250, issued Aug. 21, 1990 to Terry M. Haber and John A. Lewis, discloses a collapsible needle cover which requires two hands to operate with one of the hands being located in the vicinity of the needle.

SUMMARY AND OBJECTS OF THE INVENTION

It is an object of this invention to provide a disposable, safety syringe having a means for protecting the user from accidental pricks by a used needle.

It is a further object of this invention to provide a disposable syringe with a means for sealing both the needle end and the plunger end from accidental loss of body fluid which may be contained therein subsequent to use of the syringe.

It is still another object of this invention to provide a disposable syringe with a means for sealing both ends of the syringe which may be simply and reliably operated by one hand.

It is an additional object of this invention to provide a disposable syringe having a sheath wherein the needle is withdrawn into a sheath use after by shifting the syringe relative to the sheath rather than vice versa as in the prior art.

These and other objects are achieved by providing a conventional syringe with a sheath which is of a size to substantially enclose the syringe, the sheath being connected to the syringe by a compression spring suitably connected to the sheath and to a flange of the syringe. The connection to the sheath includes a rubber washer or gasket glued to the sheath and to one end of the spring Which encircles the syringe. Also provided on the sheath is a spring biased latch engaging the end of the compression spring attached to the syringe flange or alternatively, a peg and detent latch molded into the syringe cylinder and surrounding sheath. During use, the syringe remains enclosed within the sheath by these latches with the needle mounting end extending through an opening at the base of the sheath, the needle being interchangeably mounted through a threaded connection. Also mounted at the opening is a spring biased pivotally mounted plate which bears on the needle mounting end of the syringe during use. Prior to disposing the used syringe the user need do no more than depress the plunger of the syringe with a little more than the normal force whereby the flange disengages the latch means from the compression spring, thereby enabling the compression spring to push the syringe in a direction of movement out of the sheath, thereby moving the needle into the sheath, allowing the spring biased plate to close the opening at the base of the sheath. The seal produced by the washer or gasket at one end and the spring biased plate at the other end need not be air tight, and therefore the gasket and spring biased plate may be formed of spongy material if desired for the purpose of absorbing excess leaking fluids still contained in the syringe after use. After sealing the syringe and sheath connected thereto may be safely disposed of without endangering the user or subsequent handler.

Other objects, features and advantages of this invention will become apparent from the following detailed description of the appended claims, reference being had to the accompanying drawings forming a part of the specification, wherein like reference numerals designate corresponding parts of the several views.

BRIEF DESCRIPTION OF THE DRAWINGS

FIG. 4 is an exploded perspective view of the sheath and cylinder of the disposable safety syringe showing another embodiment of the latch.

FIG. 5 is a detail view of FIG. 4.

DETAILED DESCRIPTION OF THE PREFERRED EMBODIMENTS

Before explaining in detail the present invention, it is to be understood that the invention is not limited in its application to the details of construction and arrangement of parts illustrated in the accompanying drawings, since the invention is capable of other embodiments and of being practiced or carried out in various ways. Also it is to be understood that the phraseology and terminology employed herein is for the purpose of description and not limitation.

Figure 1:
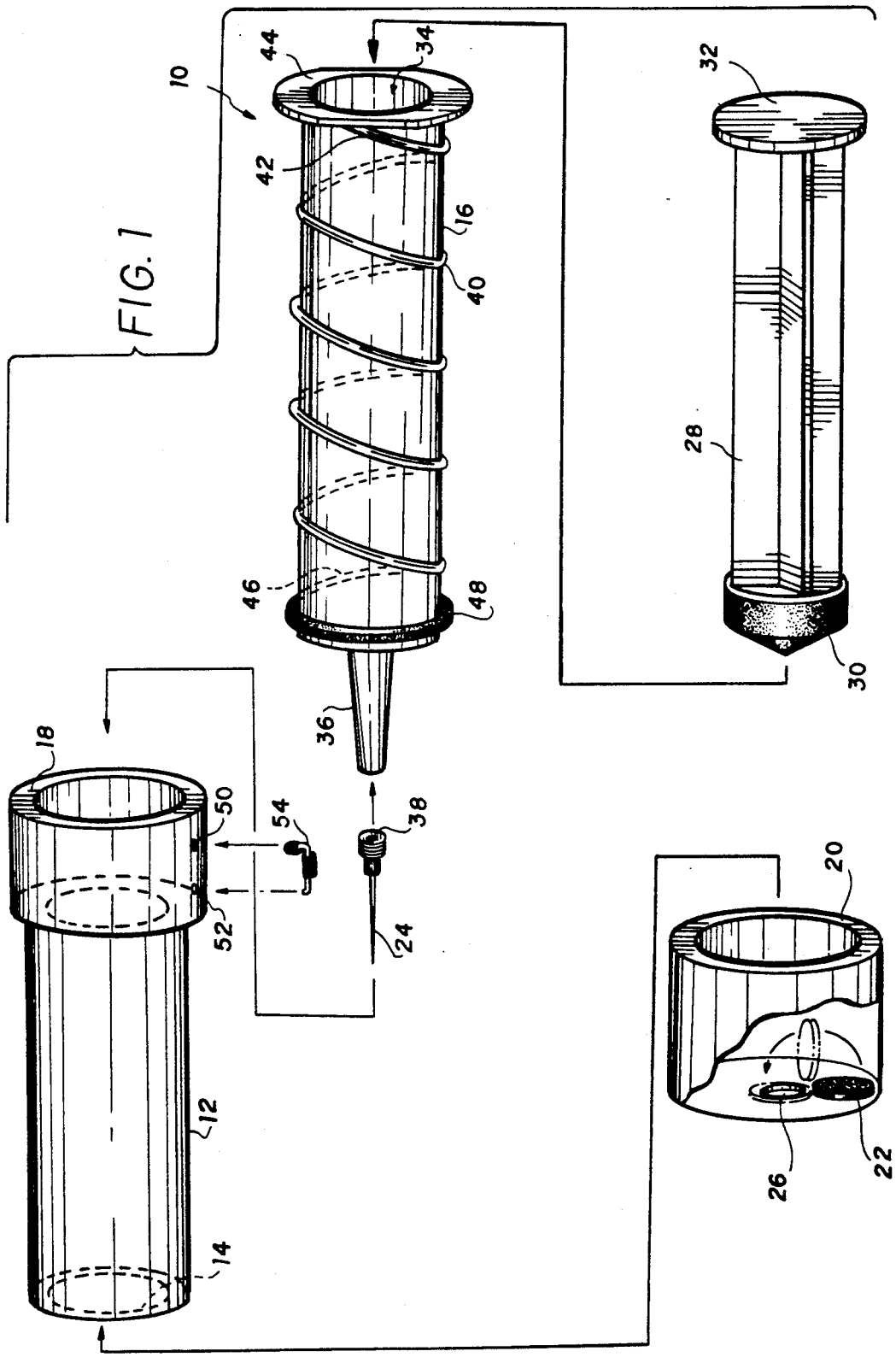
FIG. 1 is an exploded perspective view of the component parts of the disposable safety syringe showing one embodiment of the latch.

FIG. 1 shows the component parts of the disposable safety syringe 10 in an exploded fashion. Protective sheath 12 is shown to have a cylindrical configuration with a central opening 14 with a diameter sufficient to allow the cylinder 16 of a conventional syringe to slidably fit therein. Sheath 12 is topped by a cup portion 18 having a larger inner and outer diameter than sheath 12 for a purpose described below. Cap portion 20 fits on the base of sheath 12 and includes a spring biased pivotally mounted disc 22 which, when the needle 24 is withdrawn into sheath 12 as explained below, snaps over opening 26 to seal opening 26. Cap portion 20 may be either a separate element suitably attached to sheath 12, or formed integrally with sheath 12 if desired.

Cooperating with cylinder 16 is a plunger 28 having a sealing piston 30 at one end and a thumb or depressor place 32 at the other end. Plunger 28 is shiftable in the internal bore 34 of cylinder 16 so as to draw fluid into cylinder 16 or to expel fluid from cylinder 16. At the opposite end of cylinder 16 needle mount 36 may be internally threaded as shown in FIGS. 2 and 3 so as to interchangeably mount needles 24 threaded as at 38.

Surrounding cylinder 16 is a large compression spring 40. One upper end 42 of spring 40 is fixedly attached to flange 44 of cylinder 16 by gluing or by conventional mechanical means. The other, lower end 46 of spring 40 is similarly fixedly attached to a rubber gasket or o-ring 48 which is also fixedly attached to the base of cup portion 18 as shown in FIGS. 2 and 3.

Figure 2:
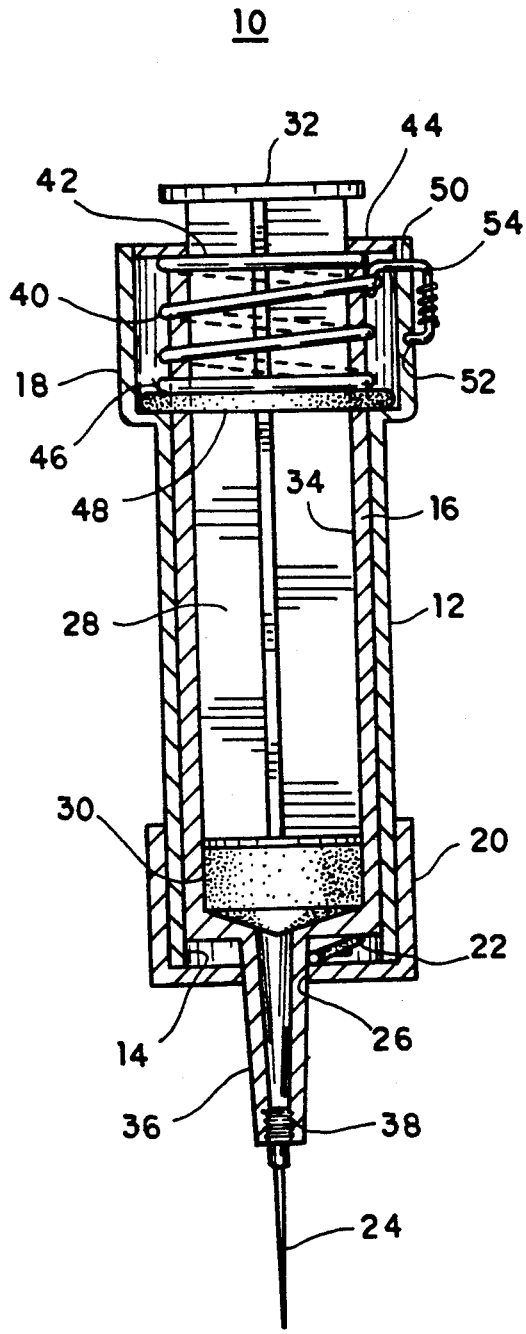
FIG. 2 is a cross-sectional view of the disposable safety syringe prior to use.
Figure 3:
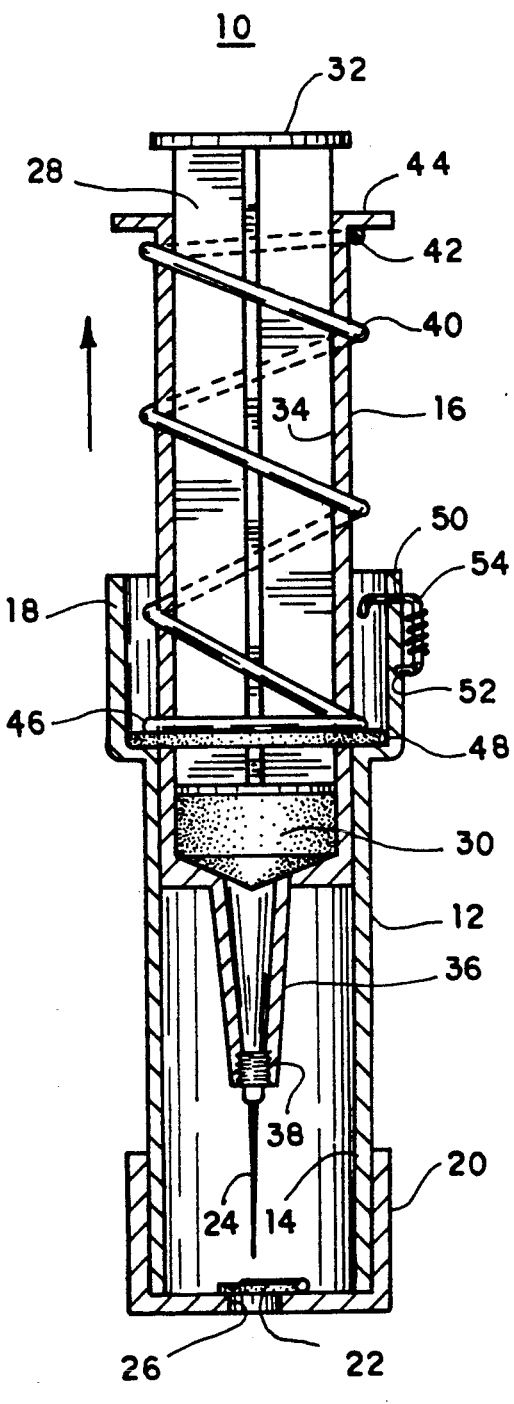
FIG. 3 is a cross-sectional view of the disposable safety syringe subsequent to use with the syringe needle withdrawn into the sheath prior to disposal.

Mounted in holes 50 and 52 of the sidewall of cup portion 18 is a spring biased latch 54, the purpose of which is to latch spring 40 and accordingly cylinder 16 in the downward position within sheath 12 prior to and during the use of syringe 10, as shown in FIG. 2. This places needle 24 in an operational position allowing fluid to be drawn into or expelled from cylinder 16 as desired. Also, needle 24 may be exchanged for another needle as needed or desired.

An alternate embodiment, as shown in FIGS. 4 and 5, employs a different latch 60 comprising a peg 62 which is held by a detent 64.

The peg 62 is molded integrally with or firmly attached to the flange 44 of the cylinder 16. The flange 44 is wide enough to support the force of the spring 40.

The detent 64 has a recess generally in the shape of an inverted U. It protrudes from the inside surface of the cup portion 18 far enough that the peg 62 can be held within the U of the detent: that is, when the cylinder 16 is slid into the sheath 12, the peg 62 will interfere with the protruding parts defining the U, but will not interfere with the areas of the cup portion 18 inside or outside of the U.

The force of the spring 40, when the syringe is assembled and the peg 62 is within the U of the detent 64, holds the peg therein and prevents the cylinder 16 from sliding out of the sheath 12. To release the cylinder 16, it will need to be pushed inward against the spring 40 and the cylinder 16 rotated slightly to clear the detent 64. However, this is awkward or impossible to do with one hand. Therefore, the spring 40 is twisted as well as compressed in this embodiment to automatically release the peg 62 from the detent 64 when the cylinder is merely pushed into the sheath 12.

As seen in FIG. 4, the lower end 46 of the spring 40 is held to the gasket 48 as in the first embodiment. Other attachment means are possible. For example, the lower end 46 could be held to the cup portion 18 by having its lower end 46 bent sharply over and inserted into a hole through the wall of the cup portion 18 (not shown). This would locate the lower end 46 both axially and rotationally. The upper end 42 of the spring 40 could also be bent upward and wrapped over the peg 62. The end 42 would thus be held against rotation in one direction.

It will be seen that, if the ends 42 and 46 of the spring 40 are angularly located relative to one another at a first angle, and the attachment of the lower end 46 of the spring 40 and the detent 64 are also located at a second angle, it is possible to load the spring 40 into the cup portion so that the spring 40 is twisted and is exerting a torque between the cylinder 16 and sheath 12. If the spring 40 is so twisted, then when the cylinder 16 is pushed firmly into the sheath 12, the peg 62 will clear the U of the detent 64, the cylinder 16 will rotate under the torque of the spring 40, and the peg 62 will be in a position where it is clear of the detent 64; the spring 40 can then force the cylinder 16 out of the sheath 12 to retract the needle 24.

When syringe 10 is to be disposed of, the user need only depress plate 32 a little bit further allowing upper end 42 of spring 50, or flange 44, to engage an end of latch 54 so as to cam latch 54 away from spring 40, enabling spring 40 to push against flange 44 to raise cylinder 16 out of sheath 12 as shown in FIG. 3. Needle 24 in turn is pulled into sheath 12, allowing spring biased disc 22 to close opening 26 sealing the cap portion 20 of sheath 12. Gasket or o-ring 48 functions to seal the other end of sheath 12 thereby effectively trapping any fluids Which may leak out through needle 24 within the sheath. Syringe 10 may now be safely disposed of without endangering anyone who might handle syringe 10 during its disposal. It should be noted that the seals need not be air-tight. Elements 22 and 48 may incorporate spongy material if desired to soak up excess fluid which might leak into sheath 12.

While it will be apparent that the preferred embodiment of the invention herein disclosed is well calculated to fulfill the objects stated above, it will be appreciated that the invention is susceptible to modification, variation and change without departing from the proper scope or fair meaning of the subjoined claims.

It is to be understood that the present invention is not limited to the sole embodiment described above, but encompasses any and all embodiments within the scope of the following claims.

I claim:

1. A disposable safety syringe comprising:
   a sheath means having an opening for slidably receiving a syringe means therein;
   a syringe means slidably received in said sheath means;
   needle means extending from said syringe means;
   latch mean holding said syringe means in operative position within said sheath means;
   means for sealing said needle means within said sheath means after said latch means is released prior to disposal of said safety syringe; whereby handlers of said safety syringe are protected from accidental pricks by said needle means subsequent to use thereof;
   said sheath means comprising a central elongated cylinder means having a longitudinal opening therethrough, an upper cup means having a base means integral with said central elongated cylinder means and having a longitudinal opening therein communicating with and having a larger diameter than the longitudinal opening of said central elongated cylinder means, and a lower cap means having a small diameter opening therein for said needle means;
   said syringe means comprising an elongated cylinder means slidable in the longitudinal opening of said central elongated cylinder means of said sheath means at one end and a depressor plate means at the other end, said plunger means insertable in said elongated cylinder means of said syringe means, and a needle mount means at the base of said elongated cylinder means of said syringe means, said needle means being mounted in said needle mount means; and
   said sealing means comprising a compression spring means surrounding said elongated cylinder means of said syringe means, one end of said compression spring means being attached to an upper flange means of said elongated cylinder means of said syringe means, a lower end of said compression spring means being attached to a gasket means surrounding said elongated cylinder means of said syringe means, said gasket means also being attached to said base means of said upper cup means of said sheath means, said latch means to engage and retain said compression spring means in a compressed state and thereby retaining said syringe means within said sheath means in an operational mode, said cap means having a spring biased pivoted disc means effective to cover and seal said small diameter opening therein when said needle means is withdrawn into said sheath means; whereby when it is desired to dispose of said safety syringe a user depresses said depressor plate and said syringe means in said sheath means to an extent sufficient to release said latch means, thereby enabling said compression spring means to expand sufficiently to raise said syringe means in said sheath means and to withdraw said needle means into said sheath means, enabling said disc means to seal said small diameter opening, while said gasket means provides a seal above said needle means by cooperating with said elongated cylinder means of said syringe means, said user being protected against accidental needle pricks during disposal of said safety syringe.

2. A disposable safety syringe as in claim 1 said needle mount means and said needle means having mating threads thereon, whereby said needle means may be readily interchanged with another needle means.

3. A disposable safety syringe as in claim 1, said gasket means and said disc means including spongy material to absorb liquids which may leak from said needle means after sealing thereof.

4. A disposable safety syringe as in claim 1, wherein said latch means is attached to a sidewall of said upper cup means and is spring biased to engage said upper end of said compressions spring means.

5. A disposable safety syringe as in claim 1, wherein said latch means includes:
   peg means extending from said flange means;
   detent means including a U-shaped cavity for accepting internally said peg means and preventing said peg means from exiting said cavity in a direction of retraction of said cylinder means of said syringe means from said sheath means, and allowing said peg means to exit from said cavity in a direction of insertion of said cylinder means of said syringe means into said sheath means; and
   spring torque biasing means for twisting said spring means when said peg means is inserted into said detent means; whereby
   when said cylinder means of said syringe means is inserted fully into said sheath means, said peg means exits said detent means and said cylinder means of said syringe means is twisted relative to said sheath means by said spring means, so that said cylinder means of said syringe means retracts from said sheath means to withdraw said needle means into said sheath means.

* * * * *